United States Patent [19]

Metcalfe

[11] Patent Number: 4,863,778
[45] Date of Patent: Sep. 5, 1989

[54] PRODUCTS, PROCESSES AND USE
[75] Inventor: Peter J. Metcalfe, Cottingham, United Kingdom
[73] Assignee: Smith and Nephew Associated Companies p.l.c., United Kingdom
[21] Appl. No.: 487,219
[22] Filed: Apr. 21, 1983
[30] Foreign Application Priority Data Apr. 24, 1982 [GB] United Kingdom ............... 8211913

[51] Int. Cl.$^4$ .......................... A61L 15/06; C08J 5/18
[52] U.S. Cl. .................................... 428/131; 428/137; 428/304.4
[58] Field of Search ............... 428/131, 132, 134, 135, 428/136, 137, 423.1, 227, 304.4; 128/156, 334 R, 335, 335.5

[56] References Cited

U.S. PATENT DOCUMENTS

| | | | |
|---|---|---|---|
| 2,096,564 | 10/1937 | Scholl | 128/156 |
| 2,115,122 | 4/1938 | Prudden | 128/156 X |
| 3,486,968 | 12/1969 | Mater | 128/156 |
| 3,543,750 | 12/1970 | Meizanis | 428/161 X |
| 4,133,310 | 1/1979 | Lloyd et al. | |
| 4,135,023 | 1/1979 | Lloyd et al. | |
| 4,140,826 | 2/1979 | Liu | 428/910 X |
| 4,370,981 | 2/1983 | Sanderson | 128/335 X |

FOREIGN PATENT DOCUMENTS

| | | |
|---|---|---|
| 0006263 | 1/1980 | European Pat. Off. |
| 0046071 | 2/1982 | European Pat. Off. |
| 0050514 | 4/1982 | European Pat. Off. |
| 0059049 | 9/1982 | European Pat. Off. |
| 1142323 | 2/1969 | United Kingdom |

Primary Examiner—Nancy A. B. Swisher
Attorney, Agent, or Firm—Jacobs & Jacobs

[57] ABSTRACT

The present invention is directed to an elastic apertured film which contains voids. The film comprises a blend of polyurethane and an incompatible polymer which forms a discrete phase within the matrix of polyurethane. The film is in the form of a net. The area of apertures is 5 to 75% of the total area of the film or alternatively, the film is in the form of an interrupted film containing a pattern of holes which have a maximum dimension of not more than 3 times the thickness of the film.

8 Claims, No Drawings

PRODUCTS, PROCESSES AND USE

The present invention relates to elastomeric apertured films, the processes for the preparation and their use.

British patent application No. 2081721A disclosed that voided moisture vapour permeable films could be prepared that were suitable for use in the preparation for medical dressings. One of the virtues of such films was that they could be used to provide egress of moisture vapour from the skin without permitting ingress of bacteria. It has now been discovered that the materials disclosed in said application can be provided in the form of elastic apertured films which, while they cannot be used to prevent ingress of bacteria, can nevertheless be used for a wide variety of purposes including use in elastic bandages, elastic garments and wound dressings.

The present invention provides elastic apertured films comprising a blend of polyurethane and an incompatible polymer which forms a discrete phase within the matrix of polyurethane.

Preferred blends of polymers for use in this invention are as described in British patent application No. 2081721A the disclosure of which is incorporated herein by cross reference.

In a first highly favoured aspect the elastic apertured film of this invention is in the form of a net. When used herein the term "net" means a structure having a set of parallel ribs. More suitably the nets of this invention will have at least two sets parallel ribs which sets intersect each other. Most suitably the nets of this invention will have two sets of parallel ribs which sets are perpendicular to each other.

The nets of this invention will frequently contain membranes extending outwardly from the ribs to define the aperture. Whether the aperture is defined by such membranes or by the ribs per se, it is believed that the area of aperture to the total area of the film is suitably 5 to 75%, more suitably 10 to 50% and is preferably 20 to 40%.

Nets of this invention will suitably contain at least one set of ribs which are from 0.05 to 2.5 mm thick, more suitably 0.1 to 1 mm and preferably from 0.2 mm to 0.5 mm thick.

The nets of this invention may be prepared by forming a film having thicker and thinner areas and stretching that film until appertures are formed. During stretching voiding of the film occurs (see afore mentioned British patent application) which is then followed by rupture of the thinner areas to form appertures.

Generally overall thickness of the embossed film will be from 0.15 to 7.5 mm thick, more suitably from 0.25 to 3.5 mm thick and preferably from 0.5 mm to 0.15 mm thick. More suitably the thinner part of the film employed will be from 0.02 mm to 0.5 mm thick, more suitably from 0.010 mm to 0.075 mm thick and preferably from 0.005 mm to 0.1 mm thick.

The pattern of thicker and thinner areas provided on the film to be stretched will be chosen to ensure that undue propegation of the rupture will be prevented. Suitable patterns thus include those set forth in British Patent Nos. 914489, 1055963, 1075487 and 1110051.

The nets of this invention may be used as found facing layers, elastic components in elastic bandages, elastic stockings, ladies foundation garments, wound facing layers and the like.

In a second highly favoured aspect the apertured film of this invention is in the form of an interupted film. When used herein the term "interupted" means that the film contains a pattern of holes which holes have a maximum dimension of not more than 3 times the thickness of the film. Most aptly the holes have a maximum dimension of not more than the thickness of the film and preferably not more than half the thickness of the film.

Aptly the area of the holes to that of the total area of the film is from 0.05 to 4.5%, more aptly from 0.1 to 2% and preferably from 0.5 to 1.5%, for example 1%.

The holes may suitably have an approximately eliptical shape (for a uniaxially stretched film) or an approximately circular shape (for a biaxially stretched film).

The interupted films of this invention may be used as backings in first aid dressings, for example by employing an adhesive as described in British Patent Application No. 2081721A.

The apertured films of this invention may be made by using methods known in the art to be suitable when employing non-elastomeric materials such as polyolefines, for example polyethylene. It is one of the surprising qualities of the polymer blends disclosed in British Patent Application No. 2081721A that can be processed by such methods since it has herebefore been generally believed that elastomeric materials could not be processed in such manner.

The following Examples illustrate the invention.

Example 1

Extrusion Compound Preparation

An extrusion feedstock was prepared as follows:

(i) 60 parts by weight of thermoplastic polyurethane (PU) polymer granules (Estane 58201, supplied by B. F. Goodrich Ltd.), were combined with 40 parts by weight of High Impact polystyrene (HIPS) granules (Styron 485, manufactured by the Dow Chemical Col Ltd., and supplied by R. H. Cole Ltd., reference 6MW), and the resultant mixture introduced into a rotary tumble blender, which was operated for ten minutes to ensure that a sufficiently even dispersion of one type of granule in the other had been obtained for the efficient operation of the next stage of the process.

(ii) The mixture of granules from (i) was loaded into the hopper of a Reifenhauser S60 60 mm extruder. This extruder was equipped with a multirod die which had 12 circular outlet channels, each 3 mm in diameter. The extruder was also equipped with a polyolefin type screw which had a length to diameter ratio of 20:1 and a compression ratio of 3:1.

The extrusion was carried out using a die temperature of 185° C. and a screw speed of 38 rpm. The filaments produced were drawn through a water bath maintained at 20° C. at a speed sufficient to reduce their diameters to approximately 2 mm. After travelling a distance of 1 meter through this bath the filaments were passed through a chamber equipped with a hot air blower, to removed excess moisture before being cut into 3–5 mm lengths using a laboratory model granulator (Accrapak).

The granules were collected from the granulator and then dried for four hours at 90° C. in air circulating ovens in trays 2.5 cm deep.

Film Extrusion

The dried compound prepared above was used to produce an embossed film as follows:

The compound was fed into the hopper of a Reifenhauser S60, 60 mm extruder equipped as above, with the exception of the die, which in this case was a 600 mm wide flat film flexible lip die set to a gap of 0.254 mm and maintained at a temperature of 185° C. Using a screw speed of 36 rpm, a melt film was extruded vertically downwards and fed into the nip of a two roller chill casting unit located directly below the die at a distance of 13.75 cm.

One roller of this chill casting unit (9) was provided with one circumferential groove per transverse millimeter defined between flat topped roller ridges with, in cross section, 45° inwardly tapering sides. The flat tops of the ridges had a width of 0.203 mm. The film was taken off over this roller, which was maintained at a temperature of 40° C. The other roller (8) was provided with one axial groove per circumferential millimeter, having the same geometry and dimensions as those provided in the other roller (9). This roller was maintained at a temperature of 65° C.

At a nip casting speed of 1/4 m/min, the film produced was 465 mm wide, had an overall thickness of 0.89 mm and a weight of 470 gsm. It had on one surface one longitudinal rib per 0.975 mm (measured in the transverse direction), and a result of contact with the roller (9).

The opposed surface had one transverse rib per 1.15 m (measured in the machine direction) as a result of contact with roller (8).

The continuous membranes remaining between the points of intersection of the two sets of ribs were approximately rectangular in shape, having dimensions of 0.23 mm × 0.20 mm, the smaller dimension being parallel to the machine direction and thickness of 0.052 mm.

At the base of the ribs, i.e. where they formed the boundaries of the membranes, their widths were 0.78 mm (longitudinal ribs) and 0.60 mm (transverse ribs).

Film Stretching

A sample of the above grooved sheet, 100 mm wide, was gripped in the jaws of a laboratory Hounsfield tensometer so as to have a gauge length of 80 mm and with the longitudinal ribs parallel to the proposed direction of stretching.

The stretching operation was then carried out, at 20° C., with the jaws separating at a rate of approximately 100 mm per minute. In this manner the grooved sheet was stretched until a stretch ratio of 2.5:1 had been attained, by which stage the membrane had split and become apertured. The apertured sheet was then allowed to contract. A sample of the deformed portion was then stretched in a similar manner in the direction which was perpendicular to the above stretch direction, until a stretch ratio of 4:1 was achieved. The film was again allowed to contract.

The net produced by the above operations was 0.79 mm in overall thickness and had a weight per unit area of 280 gsm.

The apertures in this net were essentially elliptical in shape, the larger axis being aligned in the direction which was the transverse direction in the unstretched film. The maximum dimensions of the apertures were 0.73 and 0.31 mm. The distance between centre points of the apertures was 1.36 mm in the direction which had been the machine direction in the unstretched film and 1.22 mm in the direction perpendicular to this.

Example 2

The extrusion compounding of the component materials (which were the same as in Example 1) extrusion of the film and the film produced were all as in Example 1.

The stretching procedure was the same as in Example 1, with the exception that the transverse stretching was carried out first. The draw ratios attained were 3:1 m in both the transverse and machine directions.

The dimensions of the net obtained were as follows:
Overall thickness: 0.81 mm
Weight: 315 gsm
Aperture deminsions:
Major Axis, (transverse direction): 0.75 mm
Minor Axis, (machine direction): 0.57 mm
Distance between centre points: 1.73 mm Machine Direction 1.24 mm Transverse Direction Example 3

The extrusion compounding of the component materials and the extrusion of the film were carried out in Example 1 with the exception that roller (8) was provided with one axial groove per 0.635 mm defined between flat topped roller ridges with, in cross section, 450 inwardly tapering sides. The flat tops of the ridges had a width of 0.125 mm. This roller was maintained at a temperature of 65° C.

At a casting nip speed of 2.0 m/min the film produced was 465 mm wide, had an overall thickness of 0.58 mm and a weight of 305 gsm. The film was of similar appearance to that produced in Examples 1 and 2. The longitudinal ribs had a frequency of one per 1.0 mm measured in the transverse direction, whilst the transverse ribs had a frequency of one per 0.706 mm measured in the machine direction. The membrane dimensions were 0.28 mm × 0.2 mm × 0.05 mm thickness; the largest dimension being parallel to the transverse direction. At the base of the ribs their widths were 0.64 mm (longitudinal ribs) and 0.48 mm (transverse ribs).

The stretching procedure was the same as in Example 1, except that the temperature used was 60° C. and the draw ratios attained were 3:1 in the machine direction and 3.5:1 in the transverse direction.

The dimensions of the net obtained were as follows:
Overall thickness: 0.46 mm
Weight: 115 gsm
Aperture dimensions:
Major Axis, (transverse direction): 0.65 mm
Minor Axis, (machine direction): 0.38 mm
Distance between centre points: 1.32 mm Machine direction, 1.31 mm Transverse direction Example 4

The extrusion compound was prepared as in Example 1 from the same constituent materials.

The compound was fed into the hopper of a Brabender Extrusiograph instrumented extruder, which was driven by a Brabender Plasticorder PLE 651 drive unit and which was equipped with a 150 mm wide flat sheet die and a polyolefin-type screw with a length to diameter ratio of 25:1 and compression ratio of 3:1. The die was maintained at a temperature of 185° C. and, using a screw speed of 60 rpm, which gave registered torque and axial back pressure measurements of 68 Nm and 3 KN respectively, a melt film was extruded longitudinally and fed into the nip of a two roller chill casting unit located 5 cm from the die face.

One roller of this chill casting unit (4) was provided with one conical projection per 0.725 mm in both circumferential and axial roller directions. The height of these projections above the roller surface was 0.21 mm and their diameter at the roller surface was 0.42 mm.

The other roller in the chill casting unit (3) was a flat surfaced, rubber coated roller. The casting nip speed was 4.0 meters/minute. The film produced was 72 mm wide, had a thickness of 0.119 mm and had a weight per unit area of 114 gsm.

This film had a series of depressions in one surface, which were approximately conical in nature. Where the depressions interrupted the surface of the film, their diameter was 0.07 mm. Their depth was such that the film was not perforated. Their centre to centre separation was 0.75 mm measured in both machine and transverse directions.

A full width sample of this film was gripped in the jaws of a laboratory Hounsfield tensometer so as to have a gauge length of 80 mm and with the machine direction parallel to the proposed direction of stretching.

The stretching conditions used were as in Example 1, and a stretch ratio of 3.25:1 was attained in the machine direction after which the film was allowed to contract. During this stretching procedure interruptions were formed, associated with the depressions in the film.

In the relaxed film these interruptions were elliptical in shape where they intersected the surface of the film, which had been in contact with the embossing roller during casting, their dimensions being 0.19×0.069 mm, with the larger dimension being aligned approximately parallel to the stretching direction.

The centre to centre separation of these interruptions, as measured in the plane of the surface which had been in contact with the embossing roller, was 1.24 mm in what had been the machine direction during extrusion and 0.57 mm in the direction perpendicular to this.

The film thickness was 0.107 mm and the film weight per unit area was 81 gsm.

Example 5

The extrusion compounding of the component materials and the film extrusion were carried out as in Example 4, except that the casting nip spread was 6.0 m/min.

The film produced was 66 mm wide, had a thickness of 0.081 mm and a weight of 91 gsm. The film had a series of depressions in one surface, which were approximately conical in shape. Where the depressions interrupted the surface of the film, they were elliptical in shape with dimensions of 0.062×0.087 mm, the larger dimension being parallel to the machine direction. Their depth was such that the film was not interrupted. Their centre to centre separation was 0.80 mm, measured in the machine direction and 0.70 mm measured in the transverse direction.

The sample was stretched as in Example 4, except that a stretching ratio of only 3:1 was attained. During this stretching procedure, interruptions were formed associated with the depressions in the film.

In the relaxed film these interruptions were elliptical in shape, their dimensions being 0.06×0.16 mm, with the larger dimension being aligned approximately parallel to the stretching direction.

The centre to centre separation of these interruptions as measured in the plane of the surface which had been in contact with the embossing roller, was 1.00 mm in what had been the machine direction during extrusion and 0.62 mm in the direction perpendicular to this.

The film had a weight per unit area of 53 gsm and a thickness of 0.063 mm.

Example 6

Extrusion Compound Preparation

An extrusion feedstock was prepared as follows:

(i) 60 parts by weight of thermoplastic polyurethane (PU) polymer granules (Estane 58201, supplied by B. F. Goodrich Ltd.), were combined with 40 parts by weight of low density polyetrylene purge compound (British Petroleum Ltd.), and the resultant mixture introduced into a rotary tumble blender, which was operated for ten minutes to ensure that a sufficiently even dispersion of one type of granule in the other had been obtained for the efficient operation of the next stage of the process.

(ii) The mixture of granules from (i) was loaded into the hopper of a Reifenhauser S60 60 mm extruder. This extruder was equipped with a multirod die which had 12 circular outlet channels, each 3 mm in diameter. The extruder was also equipped with a polyolefin type screw which had a length to diameter ratio of 20:1 and a compression ratio of 3:1.

The extrusion was carried out using a die temperature of 185° C. and a screw speed of 38 rpm. The filaments produced were drawn through a water bath maintained at 20° C. at a speed sufficient to reduce their diameters to approximately 2 mm. After travelling a distance of 1 meter through this bath the filaments were passed through a chamber equipped with a hot air blower, to remove excess moisture before being cut into 3-5 mm lengths using an Accrapak model laboratory granulator.

The granules were collected from the granulator and then dried for four hours at 90° C. in air circulating ovens in trays 2.5 cm deep.

Film Extrusion

The dried compound prepared above was used to produce an embossed film as follows:

The compound was fed into the hopper of a Reifenhauser S60, 60 mm extruder equipped as above, with the exception of the die, which in this case was a 300 wide flat film flexible lip die set to a gap of 305 mm and maintained at a temperature of 185° C. Using a screw speed of 18 rpm, a melt film was extruded vertically downwards and fed into the nip of a two roller chill casting unit located directly below the die at a distance of 14.6 cm.

One roller of this chill casting unit (9) was provided with one circumferential groove per transverse millimeter defined between flat topped roller ridges with, in cross section, 45° inwardly tapering sides. The flat tops of the ridges had a width of 0.203 mm. The film was taken off over this roller, which was maintained at a temperature of 60° C. The other roller (8) was provided with one axial groove per circumferential millimeter, having the same geometry and dimensions as those provided in the other roller (9). This roller was maintained at a temperature of 70° C.

At a nip casting speed of 1.7 m/min, the film produced was 220 wide, had an overall thickness of a 0.355 mm and a weight of 248 gsm. It had on one surface one longitudinal rib per 0.98 mm (measured in the transverse direction), as a result of contact with roller (9).

The opposed surface had one transverse rib per 1.2 mm (measured in the machine direction) as a result of contact with roller (8).

The continuous membranes remaining between the points of intersection of the two sets of ribs were approximately rectangular in shape, having dimensions of 0.76 mm×0.41 mm the smaller dimension being parallel to the machine direction and thickness of 0.01 mm.

At the base of the ribs, i.e. where they formed the boundaries of the membranes, their widths were 0.57 mm (longitudinal ribs) and 44 mm (transverse ribs).

Film Stretching

A sample of the above grooved sheet, 100 mm wide, was gripped in the jaws of a laboratory Hounsfield tensometer so as to have a gauge length of 80 mm and with the longitudinal ribs parallel to the proposed direction of stretching.

The stretching operation was then carried out, at 20° C., with the jaws separating at a rate of approximately 100 mm per minute. In this manner the grooved sheet was stretched until a stretch ratio of 4:1 had been attained, by which stage the membranes had split and become perforated. The perforated sheet was then allowed to contract. A sample of the deformed portion was then stretched in a similar manner in the direction which was perpendicular to the above stretch direction, until a stretch ratio of 4.5:1 was achieved. The film was again allowed to contract.

The net produced by the above operations was 0.228 mm in overall thickness and had a weight of 99 gsm.

The apertures in this net were essentially elliptical in shape, the larger axis being aligned in the direction which was the transverse direction in the unstretched film. The maximum dimensions of the apertures were 1.04 mm and 0.81 mm. The distance between centre points of the apertures was 1.83 mm in the direction which had been the machine direction in the unstretched film and 1.59 mm in the direction perpendicular to this.

Example 7

The extrusion compounding, of the component materials (which were the same as in Example 1) extrusion of the film and the film produced were all as in Example 1.

The stretching procedure was the same as in Example 1, with the exception that the transverse stretching was carried out first. The draw ratios attained were 3:1 in both the transverse and machine directions.

The dimensions of the net obtained were as follows:
Overall thickness: 0.203 mm
Weight: 115 gsm
Aperture deminsions:
Major Axis, (transverse direction): 0.60 mm
Minor Axis, (machine direction): 0.43 mm
Distance between centre point: 1.72 mm Machine Direction, 1.27 mm Transverse Direction

I claim:

1. An elastic apertured film which contains voids which film comprises a blend of polyurethane and an incompatible polymer which forms a discrete phase within the matrix of polyurethane, said film being in the form of a net in which the area of the apertures is 5% to 75% of the total area of the film.

2. An elastic apertured film which contains voids which film comprises a blend of polyurethane and an incompatible polymer which forms a discrete phase within the matrix of polyurethane, said film being in the form of an interrupted film containing a pattern of holes which have a maximum dimension of not more than 3 times the thickness of the film.

3. A film according to claim 1 in which the area of the apertures is 10 to 50% of the total area of the film.

4. A film according to claim 1 in which the film has at least one set of ribs of 0.1 to 1 mm thick.

5. A film according to claim 1 in which the film has two sets of parallel ribs which sets are perpendicular to each other.

6. A film according to claim 2 in which the holes have a maximum dimension of not more than the thickness of the film and their area is 0.1 to 2% of the total area of the film.

7. A film according to claim 1 or 2 which comprises a blend of linear polyether urethane which is 45% to 85% by weight of the blend and an incompatible polymer which is high impact polystyrene.

8. An article for bodily contact which comprises an elastic apertured film according to claim 1 or 3.

* * * * *